(12) United States Patent
Seegerer et al.

(10) Patent No.: US 10,483,005 B2
(45) Date of Patent: Nov. 19, 2019

(54) SYSTEM AND METHOD FOR CHARACTERIZATION OF ELECTRICAL PROPERTIES OF THE HEART FROM MEDICAL IMAGES AND BODY SURFACE POTENTIALS

(71) Applicant: Siemens Healthcare GmbH, Erlangen (DE)

(72) Inventors: Philipp Seegerer, Fuerstenzell (DE); Tommaso Mansi, Plainsboro, NJ (US); Marie-Pierre Jolly, Hillsborough, NJ (US); Bogdan Georgescu, Plainsboro, NJ (US); Ali Kamen, Skillman, NJ (US); Dorin Comaniciu, Princeton Junction, NJ (US); Roch Mollero, Vallauris (FR); Tiziano Passerini, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/162,957

(22) Filed: Oct. 17, 2018

(65) Prior Publication Data

US 2019/0051419 A1 Feb. 14, 2019

Related U.S. Application Data

(62) Division of application No. 15/301,415, filed as application No. PCT/US2015/023986 on Apr. 2, 2015, now Pat. No. 10,141,077.

(Continued)

(51) Int. Cl.
*G16H 50/50* (2018.01)
*A61B 8/08* (2006.01)
(Continued)

(52) U.S. Cl.
CPC .......... *G16H 50/50* (2018.01); *A61B 5/0044* (2013.01); *A61B 5/0452* (2013.01); *A61B 6/032* (2013.01);
(Continued)

(58) Field of Classification Search
CPC .... G16H 50/50; A61B 6/5235; A61B 5/0452; A61B 6/5247; A61B 6/032; A61B 5/0044; G06F 17/5009; G09B 23/288; G09B 23/30
See application file for complete search history.

(56) References Cited

U.S. PATENT DOCUMENTS

2008/0177192 A1 7/2008 Chen et al.
2010/0268059 A1 10/2010 Ryu et al.
(Continued)

FOREIGN PATENT DOCUMENTS

CN 1102371 C 3/2003
CN 102346811 A 2/2012
(Continued)

OTHER PUBLICATIONS

Pfeifer et al., "Patient-Specific Volume Conductor Modeling for Non-Invasive Imaging of Cardiac Electrophysiology" The Open Medical Informatics Journal, vol. 2, No. 1, Oct. 9, 2008, pp. 32-41, XP055202998.
(Continued)

*Primary Examiner* — Anthony Ho

(57) ABSTRACT

Methods and systems for estimating patient-specific cardiac electrical properties from medical image data and non-invasive electrocardiography measurements of a patient are disclosed. A patient-specific anatomical heart model is generated from medical image data of a patient. Patient-specific cardiac electrical properties are estimated by simulating cardiac electrophysiology over time in the patient-specific (Continued)

anatomical heart model using a computational cardiac electrophysiology model and adjusting cardiac electrical parameters based on the simulation results and the non-invasive electrocardiography measurements. A patient-specific cardiac electrophysiology model with the patient-specific cardiac electrical parameters can then be used to perform virtual cardiac electrophysiology interventions for planning and guidance of cardiac electrophysiology interventions.

20 Claims, 10 Drawing Sheets

Related U.S. Application Data

(60) Provisional application No. 62/021,898, filed on Jul. 8, 2014, provisional application No. 61/973,892, filed on Apr. 2, 2014.

(51) Int. Cl.
| | |
|---|---|
| *A61B 5/00* | (2006.01) |
| *G09B 23/30* | (2006.01) |
| *G09B 23/28* | (2006.01) |
| *G06F 17/50* | (2006.01) |
| *A61B 6/03* | (2006.01) |
| *A61B 6/00* | (2006.01) |
| *A61B 5/0452* | (2006.01) |
| *G06F 19/00* | (2018.01) |
| *A61B 5/04* | (2006.01) |

(52) U.S. Cl.
CPC .......... *A61B 6/5235* (2013.01); *A61B 6/5247* (2013.01); *A61B 8/0883* (2013.01); *G06F 17/5009* (2013.01); *G06F 19/00* (2013.01); *G09B 23/288* (2013.01); *G09B 23/30* (2013.01); *A61B 5/004* (2013.01); *A61B 5/04* (2013.01); *A61B 2576/023* (2013.01)

(56) References Cited

U.S. PATENT DOCUMENTS

| | | |
|---|---|---|
| 2013/0197881 A1 | 8/2013 | Mansi et al. |
| 2013/0197884 A1 | 8/2013 | Mansi et al. |
| 2014/0012558 A1 | 1/2014 | Mansi et al. |

FOREIGN PATENT DOCUMENTS

| | | |
|---|---|---|
| WO | 2013128415 A1 | 9/2013 |
| WO | 2014038883 A1 | 3/2014 |

OTHER PUBLICATIONS

Sermesant M. et al., "Patient-Specific Electromechanical Models of the Heart for the Prediction of Pacing Acute Effects in CRT: A Preliminary Clinical Validation", Medical Image Analysis, Oxford University Press, Oxford GB, vol. 16, No. 1, Jul. 11, 2011, pp. 201-215, XP028124532.
Prakosa Adityo et al., "Cardiac Electrophysiological Activation Pattern Estimation from Images Using a Patient-Database of Synthetic Image Sequences", IEEE Transactions on Biomedical Engineering, IEEE Service Center, Piscataway, NJ, USA, vol. 1.61, No. 2, Feb. 1, 2014, pp. 235-245, XP011537366.
H. Ashikaga, "Electromechanical Analysis of Infarct Border Zone in Chronic Myocardial Infarction", AJP: Heart and Circulatory Physiology, vol. 289, No. 3, May 6, 2005, pp. H1099-HI105, XP055201908.
International Search Report and Written Opinion dated Sep. 11, 2015, in connection with International Patent Application No. PCT/US2015/023986, 17 pgs.
Chinese Office Action dated Feb. 2, 2019 in corresponding Chinese Patent Application No. 201580018052.4.
Chinese Office Action dated Jul. 18, 2019 in corresponding Chinese Patent Application No. 201580018052.4.

FIG. 4
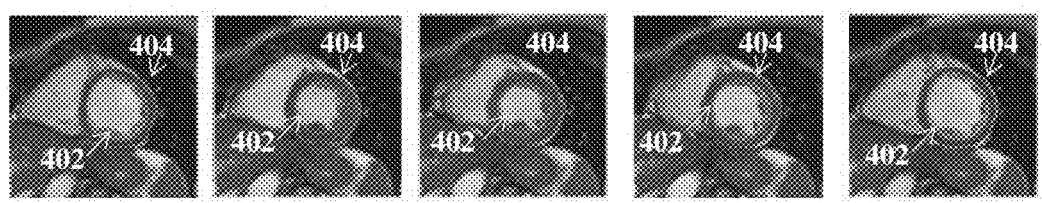
FIG. 5
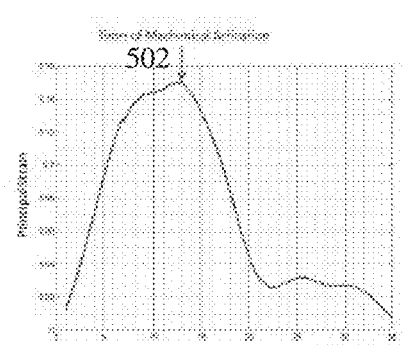
500
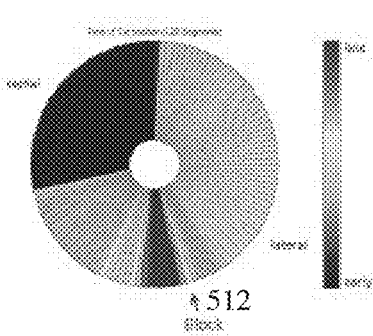
510

FIG. 6

| Algorithm 1 EP Personalization |
|---|
| Require: Initial diffusivity $c^2_{myo}, c^2_{LV}, c^2_{RV}$ and block parameters $\xi^0, \beta^0$ |
| while not converged do |
| 601 → 1: $c^*_{myo} = \text{argmin}_{c_{myo}}(\Delta_{QRS,m} - \text{calcQRS}(c_{myo}))$ |
| 602 → 2: $(c^*_{LV}, c^*_{RV}, \xi^*) = \text{argmin}_{c_{LV}, c_{RV}, \xi}(\alpha_{EA,m} - \text{calcEA}(c_{LV}, c_{RV}, \xi))$ |
| 603 → 3: $\beta^* = \text{argmin}_\beta((\Delta_{QRS,m} - \text{calcQRS}(\beta)) + 0.1 \cdot (\alpha_{EA,m} - \text{calcEA}(\beta)))$ |
| end while |

902   904   906

1002   1004

SYSTEM AND METHOD FOR CHARACTERIZATION OF ELECTRICAL PROPERTIES OF THE HEART FROM MEDICAL IMAGES AND BODY SURFACE POTENTIALS

This application is a divisional of U.S. patent application Ser. No. 15/301,415, filed Oct. 3, 2016, which is a national stage (under 35 U.S.C. § 371) of International Patent Application No. PCT/US2015/023986, filed Apr. 2, 2015, which claims the benefit of U.S. Provisional Application No. 61/973,892, filed Apr. 2, 2014, and U.S. Provisional Application No. 62/021,898, filed Jul. 8, 2014, the disclosures of which are herein incorporated by reference in their entirety.

BACKGROUND OF THE INVENTION

The present invention relates to characterization, quantification and visualization of electrical properties of the heart, and more particularly to estimating electrical properties of the heart based on an electrophysiological model of a patient from medical images and body surface potentials of the patient.

Heart failure is a major cause of death in the western world. Due to insufficient heart function, heart failure causes dyspnea and fatigue, and can also lead to cardiac arrest. Among the wide variety of cardiac rhythm disturbances, left bundle branch block (LBBB) affects approximately 25% of heart failure patients. LBBB is due to an obstruction in the cardiac conduction pathway, which decreases the speed of the electrical wave and potentially leads to dyssynchronous heart beats. For patients with a prolonged QRS-complex (e.g., QRS≥120 ms) and low left-ventricular ejection fraction, cardiac resynchronization therapy (CRT) is a well-established treatment. CRT consists of implanting electrodes in the heart to pace the muscle artificially and "resynchronize" cardiac contraction. However, 30-50% of patients do not respond to CRT despite being eligible. Hence, better patient selection for CRT is desirable.

BRIEF SUMMARY OF THE INVENTION

The present invention provides a method and system for estimating and visualizing patient-specific electrical properties of the heart from medical images and body surface potential measurements, such as classical electrocardiograms (ECG) or denser surface mapping measurements. Embodiments of the present invention utilize cardiac electrophysiology models for improved patient selection and planning of therapies like cardiac resynchronization therapy (CRT), radiofrequency ablation of atrial or ventricular arrhythmias or drug treatments. Electromechanical models can also be used without changes in the framework. To make such models clinically applicable, i.e. suitable for patient management, it is required that such models be fit to the patient patho-physiology. In other words, model parameters need to be estimated from patient data before performing virtual intervention (e.g. virtual CRT) and calculating subsequent physiology changes. Embodiments of the present invention estimate electrical parameter maps (e.g. diffusivity, action potential duration, restitution curve, etc.) of a cardiac electrophysiology or electromechanics model from medical images and electrocardiogram (ECG) or denser body surface potential mappings of the patient. While the electrical parameters can be uniform over the cardiac anatomy, embodiments of the present invention also enable the estimation of spatially varying parameters to capture local pathologies. Embodiments of the present invention then compute patient-specific cardiac electrophysiology or electromechanics simulations for therapy planning and guidance using the personalized electrical diffusivity parameters estimated for the patient.

In one embodiment of the present invention, a patient-specific anatomical heart model and a patient-specific anatomical torso model are generated from medical image data of a patient. An electrical coupling model between the patient-specific anatomical heart model and the patient-specific anatomical torso model is generated. A mechanical activation time map of the heart is generated from a dynamic cardiac image sequence of the patient. Spatially varying patient-specific cardiac electrical parameters for the patient are estimated by simulating cardiac electrophysiology over time at a plurality of nodes in the patient-specific anatomical heart model using a computational cardiac electrophysiology model and adjusting at least one cardiac electrical parameter of the computational cardiac electrophysiology or electromechanics model based on the mechanical activation time map, non-invasive electrocardiography measurements of the patient, and the simulated cardiac electrophysiology.

In another embodiment of the present invention, a patient-specific volumetric anatomical heart model and a patient-specific anatomical torso model are generated from medical image data of a patient and an electrical coupling model between the patient-specific anatomical heart model and the patient-specific anatomical torso model is generated. Extra-cellular potentials are estimated on an epicardial surface of the patient-specific anatomical heart model from measured body surface potentials on a torso of the patient based on the electrical coupling model between the patient-specific anatomical heart model and the patient-specific anatomical torso model and transmembrane potentials are estimated on the epicardial surface of the patient-specific anatomical heart model from the estimated extra-cellular potentials. Spatially varying patient-specific cardiac electrical parameters for the patient are estimated by initializing one or more cardiac electrical parameters of a computational cardiac electrophysiology model over the volumetric patient-specific anatomical heart model from the estimated transmembrane potentials on the epicardial surface of the patient-specific anatomical heart model, simulating cardiac electrophysiology over time at a plurality of nodes in the volumetric patient-specific anatomical heart model using the computational cardiac electrophysiology model, and adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology.

These and other advantages of the invention will be apparent to those of ordinary skill in the art by reference to the following detailed description and the accompanying drawings.

BRIEF DESCRIPTION OF THE DRAWINGS

FIG. 4 illustrates an example of tracking the myocardium in a sequence of cine MRI images;

FIG. 5 illustrates exemplary results of generating a mechanical activation map;

FIG. 6 illustrates an algorithm for estimating personalized electrical diffusivity parameters according to an embodiment of the present invention;

DETAILED DESCRIPTION

The present invention relates to non-invasive estimation of patient-specific electrical properties of the heart from medical imaging data and electrocardiography data of a patient and patient-specific simulation of cardiac electrophysiology for planning and guidance of cardiac therapies. Embodiments of the present invention are described herein to give a visual understanding of the methods for estimating patient-specific electrical properties of the heart and patient-specific simulation of cardiac electrophysiology from medical imaging data and electrocardiography data of a patient. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or available through a network system.

Figure 1:
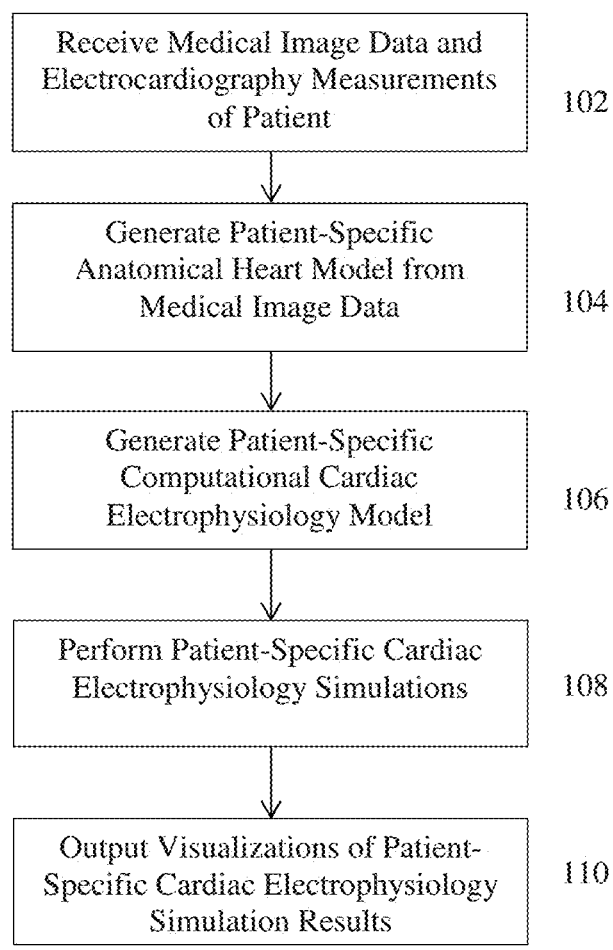
FIG. 1 illustrates a method of simulating patient-specific electrophysiology from medical image data and electrocardiography data of a patient for planning and guidance of cardiac interventions.

FIG. 1 illustrates a method of simulating patient-specific electrophysiology from medical image data and electrocardiography data of a patient for planning and guidance of cardiac interventions. The method of FIG. 1 transforms medical image data and measured electrocardiography data of a patient to determine patient-specific electrical properties of the heart and patient-specific electrophysiology simulations. At step 102, medical image data and electrocardiography measurements of a patient are received. The medical image data can be cardiac image data acquired using any type of medical imaging modality, such as computed tomography (CT), three-dimensional rotational angiography, magnetic resonance imaging (MRI), ultrasound (US), etc., provided that the heart is visible in the medical image data. In an advantageous implementation, the medical image data includes three dimensional (3D) medical image data. The medical image data can be received directly from an image acquisition device, such as a CT scanner, a C-arm image-acquisition device, an MRI scanner, or an US scanner, or the medical image data can be received by loading previously stored cardiac image data of the patient. The medical image data may be pre-operative medical image data acquired prior to a cardiac electrophysiology (EP) intervention or intra-operative medical image data acquired during a cardiac EP intervention.

The electrocardiography measurements of the patient are non-invasive measurements of potentials at particular points on the surface of the patient's body over time. The electrocardiography measurements can be measurements of potentials at points on the patient's torso. The electrocardiography measurements of the patient can be pre-operative or intra-operative. The use of pre-operative electrocardiography measurements allows a patient-specific cardiac EP model to be generated and virtual electrophysiological interventions to be performed for pre-operative planning independent of any actual intervention procedure being performed. The use of intra-operative electrocardiography measurements allows a patient-specific cardiac EP model to be generated and virtual electrophysiological interventions to be performed to guide an electrophysiological intervention in real-time or near real-time, or for intra-procedural planning. In one embodiment, the electrocardiography measurements can be electrocardiogram (ECG) measurements (12 lead, standard, etc.) of the patient. In another embodiment, the electrocardiography measurements can be body surface potential maps of the patient acquired using body surface mapping (BSM).

At step 104, a patient-specific anatomical heart model is generated from the medical image data of the patient. In order to generate the patient-specific anatomical heart model, a patient-specific heart morphology model is extracted from the medical image data. The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Papillaries and trabeculae can also be obtained, from CT images for instance. Each of these components can be used individually or jointly according to data availability and clinical application. In an exemplary embodiment, the LV and RV anatomical models estimated from the medical image data are used. In a possible implementation, only the LV and RV are explicitly modeled. In another possible implementation, models for all of the heart chambers are extracted. It is also possible that the comprehensive model including all of the heart components is extracted. The modularity of this framework enables using images in which only part of the anatomy is visible.

The anatomical model for each heart component can be extracted individually. This can be done manually through interactive contouring. Automatic or semi-automatic approaches can also be employed to facilitate the task of the operator. For instance, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

The patient-specific heart morphology model is fused into a single volumetric mesh representation and surface elements of the mesh are tagged into surface zones. For example, in the case of cardiac resynchronization therapy (CRT) or ventricular tachycardia/fibrillation (VT/VF) ablation therapy, the patient-specific LV and RV anatomical models can be fused into a single anatomical model of the bi-ventricular myocardium. In particular, the LV and RV anatomies are fused into a single volumetric mesh representation, on which vertices are tagged into surface zones (LV endocardium, LV septum, RV endocardium, RV septum) according to the underlying anatomy of the estimated surface models. According to an advantageous embodiment, tetrahedral elements can be used to accurately represent the details of the volumetric bi-ventricular anatomy. Spatial information, such as scars, grey zones, and fibrosis can be identified in images, such as late enhancement MRI. For example, the spatial information may be automatically identified using trained classifiers or may be manually identified by a clinician. The spatial information is mapped onto the volumetric mesh representing the bi-ventricular myocardium. This information is important to simulate electrical delays, electrical waves around scars, for instance, wave-reentry assessment and correctly capture impaired cardiac mechanics due to ill-functioning or dead cells.

A model of fiber orientation can be automatically calculated based on the patient-specific geometry. In an advantageous implementation, the model of fiber orientation can be automatically calculated using a rule-based approach. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, e.g., from −70 on the epicardium to +70 on the endocardium (values that can be defined by the user). Similarly, the sheet direction, which is defined by the angle $\beta$ with respect to the outward transmural axis, varies transmurally, e.g., from +45 on the epicardium to −45 on the endocardium (values that can be defined by the user). $\alpha$ and $\beta$ are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. In another embodiment, when MRI diffusion tensor imaging (DTI) is available, the fibers can be directly measured in-vivo, in the patient, using the MRI diffusion tensor imaging. In another embodiment, an atlas of cardiac fibers could be employed to register the fibers to the anatomical model. Additional details regarding generating the patient-specific anatomical heart model are described in U.S. Published Patent Application No. 2013/0197881 and U.S. Published Patent Application No. 2015/0042464, which are incorporated herein in their entirety by reference.

In addition to the patient-specific anatomical heart model, a detailed torso surface model of the patient can be extracted from the medical image data. For example, the detailed torso surface model can be extracted by automatically segmenting the patient's torso geometry from the medical image data using machine learning segmentation techniques.

At step 106, a patient-specific computational cardiac electrophysiology (EP) model is generated by estimating patient-specific cardiac electrical properties of based on the patient-specific anatomical heart model and the electrocardiograph measurements of the patient. In order to estimate the patient-specific cardiac electrical properties of the patient, cardiac electrophysiology simulations are performed using a computational cardiac EP model, and patient-specific parameters of the cardiac EP model are estimated based on a comparison of the simulated electrocardiography data resulting from the simulations and the measured electrocardiograph data of the patient. In an advantageous implementation, the patient-specific anatomical heart model provides a computational domain for solving a patient-specific electrophysiology model using the Lattice-Boltzmann method for electrophysiology (LBM-EP), which is personalized by estimating patient-specific spatially varying electrical tissue parameters, such the diffusion coefficient and action potential duration. Other electrophysiology solvers could be employed without any change in the invention, such as finite element methods, finite difference methods, and graph-based methods. The cardiac EP model is personalized once the patient-specific cardiac EP model parameters representing cardiac electrical properties of the patient are estimated. The patient-specific cardiac EP model can then be used to perform patient-specific cardiac EP simulations for planning and/or guidance of cardiac EP interventions, like CRT or ablation therapies for instance. In a possible implementation, the computational cardiac EP model can be a computational cardiac electromechanics model, which couples a computational model of cardiac biomechanics to a computational model of cardiac electrophysiology in order to simulate cardiac electrophysiology and movement of the hearty over a period of time. An advantage of using a coupled electromechanical model lays in the more accurate representation of cardiac electrophysiology during systole and diastole, i.e., when cells are all depolarized and start repolarizing, since at these stages the heart is moving, which impact the potentials that are measured on the torso surface. Alternatively, cardiac EP can be computed on a moving mesh directly obtained from a tracked segmentation in dynamic cardiac images. In this embodiment, the patient-specific heart anatomical model is calculated for all the frames of the cardiac sequence. The mesh obtained in the first frame is deformed to match the heart shape and position in the other frames. Cardiac electrophysiology is synchronously computed on the moving mesh. Two alternative embodiments for estimating cardiac electrical properties of a patient for generating a patient-specific cardiac EP model are presented below.

At step 108, patient-specific cardiac electrophysiology simulations are performed using the patient-specific cardiac EP model. In particular, transmembrane potentials are simulated at each node of the myocardium using the patient-specific cardiac EP model with the personalized cardiac electrical parameters. Extracellular potentials may be calculated based on the simulated and transmembrane potentials and torso potentials may be calculated using the extracellular potentials. In addition, a simulated ECG signal may be calculated based on the simulated torso potentials. In particular, the simulated ECG signal can be generated using the simulated torso potentials at the locations of the standard ECG leads.

Intervention planning can be performed by simulating different virtual interventions using the patient-specific cardiac EP model. Since the system is generative, cardiac electrophysiology can be computed under different virtual interventions. As a result, several therapeutic scenarios can be tested in-silico. The virtual electrophysiological interventions can be used for pre-operative planning or intra-operative guidance. For each virtual electrophysiological intervention, the transmembrane potentials, extra-cellular potentials, torso potentials, and simulated ECG signal can be simulated and displayed. Dynamic potential maps can be visualized. In order to perform a virtual intervention, one or several virtual pacing electrode locations can be received. Since the system is generative, the user (e.g., physician) can select one or more locations to virtually pace the heart, given the current estimate of the diffusivity map D(x) and the action potential duration map APD(x). The user can input one or several spatial locations for a virtual pacing electrode, for example using an input device, such as a mouse, touch screen, etc., of a computer system to select a spatial location on the anatomical heart model or one of the cardiac electrocardiography maps generated by the patient-specific cardiac EP model. In an alternative implementation, systematic virtual pacing may be automatically applied by rasterizing the model, in order to identify optimal pacing locations. In particular, a sampling scheme can be used to automatically select virtual pacing locations, and a virtual electrophysiological intervention can be performed for each pacing location. The cardiac electrophysiology is then calculated using the patient-specific cardiac EP model. In particular, a current $J_{stim}$ is added to the patient-specific cardiac EP model at the locations of the virtual pacing catheter and the cardiac electrophysiology is computed over a period of time. Each pacing electrode can pace at the same or different pacing times, according to the user choice. Such interactions can be useful for CRT or other pacing therapies, but also for ablation therapies that require entrainment pacing (e.g. VT ablation). The system also allows for virtual ablation by locally setting the tissue diffusivity to 0 to mimic the ablated lesion, or coupled to a bio heat model similar to United States Patent Publication No. 2014/0136174, which is incorporated herein by reference in its entirety.

At step 110, the simulation results can be output and visualized. For example, the simulation results can be output by visualizing dynamic electrophysiology maps (e.g., dynamic potential maps) of the simulated electrophysiology of the epicardium, endocardium, the whole myocardium volume, any layer within the myocardium, the torso, or anywhere else in the volume, and displaying these maps on a display device. In addition, 3D maps for the estimated patient-specific spatially varying parameters, such as TMP, electrical conductivity (diffusion parameters), and action potential parameters (e.g., action potential duration) can be visualized and displayed. For example, the spatially varying parameters can be visualized by color coding the mesh of the patient's anatomy. Other electrophysiological maps, such as a 3D map of depolarization times, and a 3D map of repolarization times, can also be visualized and displayed. Uncertainty calculated for the estimated myocardium electrical conductivity and action potential parameters can be also be visualized. The output simulation results can be used to plan or guide a cardiac intervention procedure. For example, the simulated cardiac electrophysiology can be used to choose one or several locations and timing of a pacing electrode or ablation catheter. In addition step, 108 can be interactively repeated such that a user inputs virtual pacing electrode locations and timing based on the cardiac electrophysiology simulation results and another cardiac electrophysiology is performed based on the user input using the patient-specific cardiac EP model.

Figure 2:
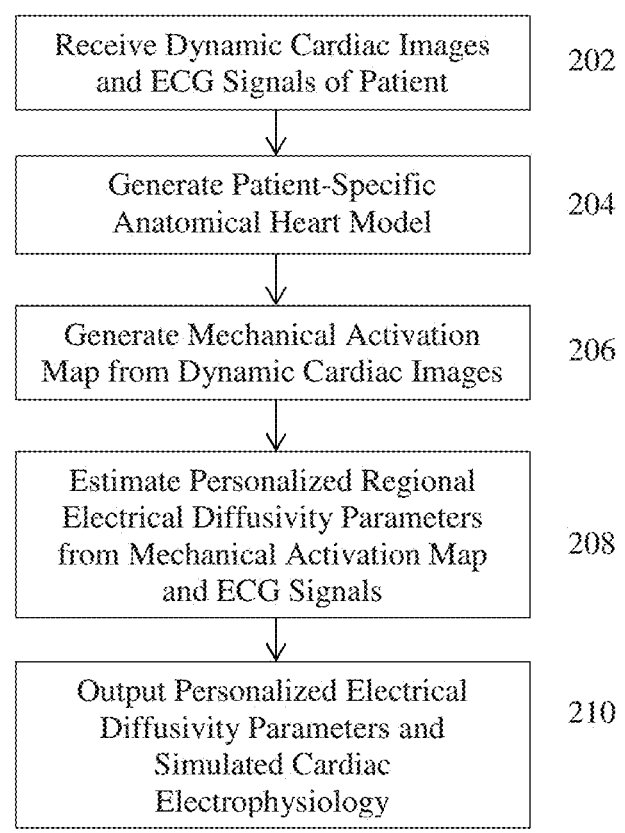
FIG. 2 illustrates a method of estimating patient-specific electrical properties of the heart according to a first embodiment of the present invention.

FIG. 2 illustrates a method of estimating patient-specific electrical properties of the heart according to a first embodiment of the present invention. The method of FIG. 2 estimates patient-specific regional electrical properties of the heart based on medical images and measured ECG signals (e.g., 12-lead ECG) of a patient. This embodiment relies on non-invasive ECG measurements and motion information gained from clinical images. While ECG features, such as QRS duration and electrical axis, provide global information of the cardiac electrophysiology, cardiac strain maps calculated from dynamic cardiac images of the patient are used to identify regional abnormalities. Mechanical activation is computed from the strain maps to identify the location of a line of block. Then, electrical diffusivity is estimated such that the resulting simulated ECG features match the measurements while the electrical depolarization pattern corresponds to the line of block. The method of FIG. 2 can be used to perform step 106 of FIG. 1 and generate a patient-specific computational cardiac EP model. Moreover, the method of FIG. 2 estimates cardiac electrical parameters of the patient that provide important information and can be employed as new physiological parameters for diagnostic and planning use, even without further simulations using the computational cardiac EP model.

Referring to FIG. 2, at step 202, dynamic cardiac images and measured ECG signals of the patient are received. In an exemplary implementation, the dynamic cardiac images can be a time sequence of short-axis stacks of cine MRI images, but the present invention is not limited thereto and other imaging modalities can be used as well, such 2D or 3D ultrasound for instance. The dynamic cardiac images can be received directly from an image acquisition device, such as an MRI scanner, or can be received by loading previously acquired dynamic cardiac images of the patient. The ECG signals can be standard 12-lead ECG signals measured from the patient. In addition, other medical image data of the patient, such as 3D cardiac images, can be received, as described in connection with step 102 of FIG. 1.

At step 204, a patient-specific anatomical model of the heart and the torso is generated from the medical image data of the patient. The patient-specific anatomical heart model is generated from medical image data of the patient, as described above in connection with step 104 of FIG. 1. As described above, the patient-specific anatomical heart model may be a detailed anatomical model of the ventricles containing fibers, scar, and other tissue information obtained from images or models. In order to generate the patient-specific anatomical model of the torso, the boundaries of the torso and optionally the lungs, muscles, and bones can be segmented in a 3D image of the torso using machine learning techniques or other image segmentation techniques. The contours representing the torso boundaries are then fused to form a volumetric 3D mesh representing the torso.

Figure 3:
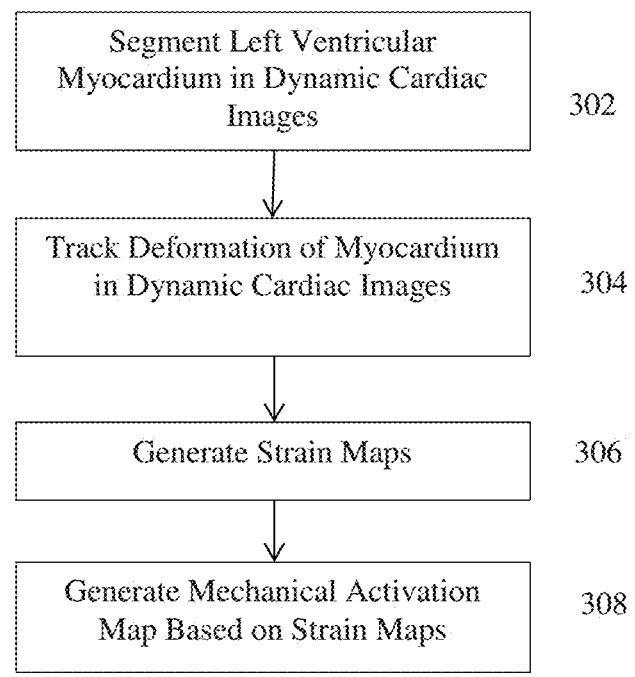
FIG. 3 illustrates a method for generating a mechanical activation map from a sequence of dynamic cardiac images according to an embodiment of the present invention.

An electrical model of diffusion in the torso is used to describe the coupling relationship between the heart and the torso. Electrical potentials on the torso can be calculated from cardiac potentials by first inferring extra-cellular potentials from the transmembrane potentials, and then solving a Poisson equation using the boundary element method (BEM), as shown in Equation (4) below. Accordingly, the electrical coupling between the heart mesh and the torso mesh can be modeled by the linear relationship $\forall t, Y_t = T^* X_t$, where $X_t(x)$ denotes the extra-cellular potentials on the epicardium, $Y_t(x)$ denotes the torso potentials, and T is the coupling matrix or "transformation matrix" obtained by boundary element discretization of the heart-torso geometry and solving for the Poisson equation for electrical potentials At step 206, a mechanical activation map is generated from the dynamic cardiac images of the patient. FIG. 3 illustrates a method for generating a mechanical activation map from a sequence of dynamic cardiac images according to an embodiment of the present invention. The method of FIG. 3 can be used to implement step 206 of FIG. 2. At step 302, the left ventricular myocardium is segmented in the sequence of dynamic cardiac images. In an exemplary implementation, the left ventricular volume can be automatically segmented in the 2D slices of the 3D cardiac images in the sequence using a 2D+time segmentation algorithm, such as the segmentation technique described in U.S. Pat. No. 8,494,236, which is incorporated herein in its entirety by reference. First, the left ventricle blood pool is automatically localized using a temporal Fourier transform and isoperimetric clustering to find the most compact and circular bright moving object in the slices. Then, the myocardium boundaries are extracted using a shortest path algorithm in polar space. Temporal consistency is enforced by backward and forward fields of an inverse consistent deformable registration, as described below in step 304. For each slice, all frames are registered by successively segmenting each frame and propagating contours to all of the other frames. The best contour set (with the least error between the projected contours and the contours segmented in the other frames) is selected as the final left ventricular myocardium segmentation.

At step 304, the deformation of the myocardium between the frames of the dynamic cardiac image sequence is tracked. The deformation of the myocardium can be tracked using 2D slice-based myocardium tracking. Deformable image registration can be performed using an inverse consistent diffeomorphic algorithm, such as the technique described in U.S. Pat. No. 8,577,177, which is incorporated herein in its entirety by reference. The registration computes a dense deformation field between any two frames in a slice without having to register every possible pair of frames explicitly. This is achieved by making the registration inverse consistent so that forward and backward deformation fields are recovered during registration of all frames to an arbitrary key frame. The deformation field between frames i and j can then be obtained by compounding the deformation filed between frames 1 and j and the inverse deformation field between frames 1 and i, where frame 1 is the key frame. For the strain computation, all time frames can be registered to the first frame. FIG. 4 illustrates an example of tracking the myocardium in a sequence of cine MRI images. As shown in FIG. 4, contours of the endocardium 402 and the epicardium 404 are tracked over time in multiple frames of a sequence of cine MRI images.

Returning to FIG. 3, at step 306, strain maps are calculated based on the myocardium deformations. The Lagrangian strain tensor E is derived from the deformation field $\Phi$, $E = \frac{1}{2}(\nabla \Phi_i + \nabla \Phi_i^T + \nabla \Phi_i \nabla \Phi_i^T)$. The principal strain, defined as the first eigenvalue of the strain tensor, is then calculated for every myocardium pixel in every frame, yielding a spatially and temporally resolved map of left ventricular strain. Basal and apical slices of the cardiac images can be excluded from the subsequent analysis due to lower image quality, but the present invention is not limited thereto. The present invention is not limited also in terms of strain quantity to use. Any other strain (longitudinal, circumferential, radial, fiber, etc.) can be used in the following.

At step 308, a mechanical activation map is generated based on the strain maps. In an advantageous implementation, a polar map of mechanical activation is defined from the calculated strains. The left ventricle is represented as a circle divided into a predetermined number (e.g., 120) segments. For each segment, the strain is averaged across the myocardium (endocardium to epicardium) and throughout the selected 2D MRI slices. If the images are 3D (e.g. using ultrasound), artificial short axis stacks can be generated at a user-defined resolution, or following the standard AHA left ventricular segmentation standard. A polar strain map is computed for each time frame for each slice. Then, the time of onset of or the time to the peak value of principal strain is identified for each segment as the time of mechanical activation. A median filter can then be applied to remove outliers. FIG. 5 illustrates exemplary results of generating a mechanical activation map. As shown in FIG. 5, image 500 shows a graph of principal strain of a single segment over time, and the time corresponding to the peak 502 of the principal strain is the time of mechanical activation. Image 510 shows a polar map of the left-ventricular mechanical activation time where the left ventricle is represented as a circle divided into 120 segments, and segment 512 shows the position of a line of block.

From the mechanical activation map, an electrical line of block is identified automatically by determining the latest activated segment. When the last activated segment is not at the lateral wall, a line of block is identified on the heart model. The position of the line of block in the myocardium is described by the circumferential angle $\xi$ with respect to the long axis of the heart. A left-endocardial voxel is considered to be inside the block if its circumferential angle ν is in a certain range around ξ. More precisely, the extent of the block is defined by the angle β around the axis identified by the circumferential angle ξ, i.e. a left-endocardial voxel is considered to be inside the block is its circumferential angle ν satisfies ν∈[ξ−0.5β; ξ+0.5β]. In addition, angular velocity can be calculated from the mechanical activation time map.

Returning to FIG. 2, at step 208, personalized regional electrical diffusivity parameters are estimated using the mechanical activation map and the measured ECG signals of the patient. In order to estimate the personalized electrical diffusivity parameters, cardiac electrophysiology and torso potentials are simulated using a computational cardiac EP model, the simulation results are compared to the measured ECG signals and the mechanical activation map, and electrical diffusivity parameters of the cardiac EP model are adjusted based on the comparison between the simulation results and the measured ECG signals and the mechanical activation map using an optimization approach. Although in the embodiment of FIG. 2, personalized regional diffusivity parameters are estimated, the present invention is not limited thereto and other cardiac electrical parameters, such as action potential duration, action potential amplitude, etc., can be calculated instead of or in addition to the electrical diffusivity parameters.

A Cartesian grid domain for electrophysiology computations is calculated using the patient-specific anatomical heart model. A Cartesian grid, usually with uniform grid spacing but also possibly with unequal and spatially varying spacing, is first generated in a bounding box surrounding the anatomical heart model. Grid spacing can be defined by the user or fixed in the system. A level-set representation is then calculated from the patient-specific anatomical mesh as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as septal nodes. Available scars and border zones are also reported in the domain through additional level-set information. Fiber orientation f(x) are mapped to each node using rasterization techniques or are recomputed from the mapped endocardial and epicardial zones directly. A diffusion coefficient c(x) and an action potential duration APD(x) is assigned to every myocardial node x of the Cartesian grid. Cell model parameters can also be mapped spatially at each node.

The cardiac electrophysiology can be simulated by calculating the transmembrane potential at each node within the myocardium using the Lattice-Boltzmann Method for Electrophysiology (LBM-EP) to solve a cardiac electrophysiology model at each node. The cardiac electrophysiology model calculates the variation of the transmembrane potential v(x,t) over time according to the mono-domain equation:

$$\frac{dv(x,t)}{dt} = R(x,t) + \nabla \cdot c(x)D(x)\nabla v(x,t), \quad (1)$$

where R(x,t) is a reaction term describing the cellular mechanisms giving rise to the action potential, c(x) is the local diffusivity to be estimated from the patient-specific data, D(x) is the anisotropy (transverse isotropy) matrix defined by $(1-\rho)f(x)f(x)^T + \rho Id$, ρ being the ratio between the cross-fiber diffusivity and the fiber diffusivity (typically ρ=0.11–0.25). It is also possible to use orthotropic or fully anisotropic tensors D(x) for improved characterization of the fiber architecture.

The choice of the reaction term R(x,t) depends on the cellular model of cardiac electrophysiology that is used. The method disclosed herein is modular in that it can handle any standard mono-domain models, such as, but not limited to the "Mitchell-Schaeffer model" proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the Mitchell-Schaeffer model for instance, we have:

$$R(x,t) = \frac{h(x,t)v^2(x,t)(1-v(x,t))}{\tau_{in}} - \frac{v(x,t)}{\tau_{out}} + J_{stim}(x). \quad (2)$$

In this equation, $J_{stim}(x)$ is an external stimulus current. In intraoperative intervention planning, when the electrophysiologist is pacing the heart at a given location, the position of the pacing electrode is tracked using an embedded tracking method (e.g., electromagnetic tracking, bi-plane image-based tracking, etc.), and the position of the pacing electrode returned by the embedded tracking method is used to add a stimulus current to the model through $J_{stim}(x)$ at the acquired position. In pre-operative planning setups, virtual pacing is achieved by adding $J_{stim}(x)$ at one or several spatial locations chosen by the user or chosen automatically by the system. The model can indeed accept one or several pacing locations without loss of generality. The amount of current that is added to the model is obtained from the catheter manufacturer specifications for instance, or manually defined. In Equation (2), h(x,t) is a gating variable that controls the state of the ion channels according to the following ordinary differential equation:

$$\frac{dh(x,t)}{dt} = \begin{cases} \frac{1-h(x,t)}{\tau_{open}} & \text{if } v(x,t) < v_{gate} \\ \frac{-h(x,t)}{\tau_{close}} & \text{otherwise} \end{cases}.$$

$V_{gate}$ is a potential threshold, and $T_{in}$, $T_{out}$, $T_{open}$ and $T_{close}$ are parameters controlling the shape of the action potential and the restitution curve.

Equation (1) is solved using the Lattice-Boltzmann method, referred to herein as LBM-EP. LBM-EP is a highly parallelizable algorithm to solve mono-domain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In order to compute the cardiac electrophysiology using LBM-EP, domain boundaries are represented as level-sets and tissue anisotropy is modeled. Since the method is node-wise, the algorithm is highly parallelizable. In an advantageous embodiment, the method can be implemented on a graphics processing unit (GPU), which enables near real-time and accurate cardiac electrophysiology computation during an intervention. In sinus rhythm, the electrocardiography model is computed with periodic stimulus at the septum to mimic the fast conducting His bundle. The electrocardiography model can be initialized with high diffusivity coefficients on the endocardia to mimic the effect of Purkinje fibers, and lower diffusivity throughout the myocardium. These initial values are then updated in one or more subsequent iterations based on the patient-specific ECG measurements and mechanical activation map as described below. It should be noted that since the framework relies on Cartesian grids, it is relatively simple to add more structural information in the model. For instance, Purkinje fibers, if available, can be added directly into the domain through rasterization. The His bundle and other electrophysiology bundles can be integrated similarly.

Once the transmembrane potentials are simulated, torso potentials are calculated based on the transmembrane potentials. An extra-cellular potential $\Phi_e$ is calculated at each node of the computational domain based on the transmembrane potential v(x,t) using a closed-form expression ($\Omega$ defines the computational domain; $|\Omega|$ is the number of elements therein):

$$\phi_e(x, t) = \frac{\lambda}{1+\lambda} \frac{1}{|\Omega|} \int_\Omega [v(y, t) - v(x, t)] dy, \quad (3)$$

where $\lambda$ is a constant diffusion anisotropy ratio, $\lambda = D_i(x)/D_e(x)$, and $D_i$ and $D_e$ are intra- and extra-cellular diffusivity tensors, respectively. The extra-cellular potential $\phi_e$ is then mapped back to the epicardium surface mesh using tri-linear interpolation. The extra-cellular potentials are then projected onto the torso surface mesh using a boundary element method (BEM). The potential $\phi(x)$ at any point x of the thoracic domain (torso surface mesh) can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[\phi_e \frac{r \cdot n}{\|r\|^3} + \frac{\nabla \phi_e \cdot n}{\|r\|}\right] dS_H, \quad (4)$$

where r is the vector defined by x and the integration point n, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. As described above, the torso mesh can be segmented from the medical image data using machine learning algorithms. According to a possible implementation, the body surface potential $\phi_b$ can be calculated for each vertex on the torso mesh. In another possible implementation, the body surface potential $\phi_b$ may be calculated only for vertices on the torso mesh corresponding to the locations of leads used to acquire the measured ECG signals (e.g., 12 lead ECG) of the patient. A simulated ECG signal is calculated using the body surface potentials calculated at the ECG lead positions, and ECG features, such as the duration of the QRS complex $\Delta_{QRS}$ and the electrical axis angle $\alpha_{EA}$ are derived automatically from the simulated ECG signal. It should be noted that in the above description a homogeneous torso model is employed. However, this can be extended to a heterogenous torso model that incorporates muscle, lungs, bones, fat and other tissues, as identified in medical images. Each tissue would then have different electrical conductivity.

The patient-specific regional electrical diffusivity parameters of the heart are estimated by iterating simulating cardiac electrophysiology and torso potentials using the computational cardiac EP model and adjusting the electrical diffusivity parameters of the cardiac EP model based on a comparison of simulation results, the measured ECG signal and the mechanical activation map. If the mechanical activation map shows an irregular pattern, i.e., the location of the latest contraction (mechanical activation) is significantly moved toward the septum and not at the lateral wall, a block in the conduction system is considered and the position and extent of the block is described by the two circumferential angles $\xi$ and $\beta$. The diffusivity of the endocardial tissue inside the block is equated with the myocardial diffusivity $c_{myo}$, because the electrical wave propagates over the myocytes as the bundle branches are obstructed. The model parameters are adjusted such that the location of the electrical fusion point matches the location of the block by setting the diffusivity for nodes in the computational domain corresponding to voxels in the block as the myocardial diffusivity $c_{myo}$ instead of the left endocardial diffusivity $c_{LV}$. Then the electrical diffusivity parameters and block parameters are estimated such that the resulting ECG features from the simulated ECG signal match the ECG features of the measured ECG signal while the simulated electrical depolarization pattern corresponds to the line of block. This can be achieved using a gradient free optimization technique, such as BOBYQA, but the present invention is not limited thereto. As described above, the patient-specific anatomical heart model can include areas labeled with particular tissue states, such as scar and border zones, which are identified using image segmentation techniques. In a possible implementation, the electrical diffusivity parameter for such areas can be constrained to a predetermined value (e.g., a value indicating little or no electrical conductivity) based on the particular tissue state.

FIG. 6 illustrates an algorithm for estimating personalized electrical diffusivity parameters according to an embodiment of the present invention. The algorithm of FIG. 6 can be used to implement step 208 of FIG. 2. In FIG. 6, calcQRS is a procedure which performs the cardiac electrocardiography and torso potential simulation using the cardiac EP model and returns the QRS duration $\Delta_{QRS}$ resulting from the EP simulation run. calcEA is a procedure which performs the cardiac electrocardiography and torso potential simulation using the cardiac EP model and returns the electrical axis angle $\alpha_{EA}$ resulting from the EP simulation run. As shown in FIG. 6, initial regional diffusivity parameters $c_{myo}^0$, $c_{LV}^0$, and $d_{RV}^0$ and initial block parameters $\xi^0$ and $\beta^0$ are input. The diffusivity parameters can be initialized with high left and right endocardial diffusivities $c_{LV}^0$ and $d_{RV}^0$ to mimic the effect of Purkinje fibers, and a lower myocardial diffusivity $c_{myo}^0$. These initial values may be standard diffusivity values from the literature. The initial block parameters $\xi^0$ and $\beta^0$ are determined from the mechanical activation map. At step 601, the myocardial diffusivity $c_{myo}$ is optimized based on the clinically measured QRS duration $\Delta_{QRS,m}$. In particular, the myocardial diffusivity $c_{myo}$ is adjusted to find the value that minimizes the difference between the measured QRS duration $\Delta_{QRS,m}$ and the simulated QRS duration. In an alternate implementation, this step may be adapted such that $c_{myo}$, $c_{LV}$, and $c_{RV}$ are all optimized based on the clinically measured QRS duration and electrical axis angle. At step 602, the fast diffusivities for the left and right endocardia $c_{LV}$ and $c_{RV}$ and the position of the line of block $\xi$ are refined based on the measured electrical axis angle $\alpha_{EA,m}$ and the strain map. In particular, the left and right endocardial diffusivities $c_{LV}$ and $c_{RV}$ and the circumferential angle $\xi$ representing the position in the block are adjusted to minimize a difference between the measured electrical axis angle $\alpha_{EA,m}$ and the simulated electrical axis angle. The position of the block is adjusted within a range around the position estimated from the mechanical activation map. The diffusivity of the "block region" is kept unchanged in this step and is equal to the estimated myocardial diffusivity $c_{myo}*$. At step 603, the block angle $\beta$ defining the extent of the block adjusted based on the measured QRS duration $\Delta_{QRS,m}$ and the measured electrical axis angle $\alpha_{EA,m}$. In particular, the block angle $\beta$ is adjusted to minimize a cost function that takes into account the difference between the measured QRS duration $\Delta_{QRS,m}$ and the simulated QRS duration and the difference between the measured electrical axis angle $\alpha_{EA,m}$ and the simulated electrical axis angle. Steps 601, 602, and 603 are iterated until convergence, resulting in personalized electrical diffusivities in the myocardium and the left and right endocardia, as well as a refined location and extent of the line of block.

As described above, in step 208, personalized regional electrical diffusivity parameters are estimated based on cardiac electrophysiology simulations using a computational cardiac EP model. According to a possible embodiment, the cardiac EP model may be computed on a moving mesh, obtained by tracking the heart on medical images. In another possible embodiment, the cardiac EP model may be a cardiac electromechanics model the couples a model of cardiac biomechanics to the model of cardiac electrophysiology to simulate cardiac electrophysiology and cardiac biomechanics (movement of the heart) over a period of time. The model of cardiac biomechanics is coupled to the model of cardiac electrophysiology described above and simulates deformation of the patient-specific anatomical model by solving the dynamics equation $M\ddot{u}+C\dot{u}+Ku=F_a+F_p+F_b$, where $\ddot{u}$, $\dot{u}$ and $u$ represent accelerations, velocities and displacements, respectively, of the mesh nodes, and M, K and C are the mass matrix, internal elastic stiffness matrix and Rayleigh damping matrix, respectively. $F_a$, $F_p$ and $F_b$ model active stress, ventricular pressure, and mechanical boundary conditions, respectively. The active stress forces $F_a$ can be computed by a model that expresses the active Cauchy stress tensor in terms of an action potential. Accordingly, the action potential computed by the model of cardiac electrophysiology at each time step for each node in the patient-specific anatomical heart model is used to determine the active stress force $F_a$ applied at that node in the model of cardiac biomechanics. The model for computing the active stress is mainly governed by three parameters, namely the maximum contraction that can be reached by a cell and the ATP binding and release rates. The model simplifies the true myocyte contraction and thus only approximates the behavior of the complex underlying bio-physical phenomena. However, this allows for the number of parameters to be rather low while clinically observable, enabling robust personalization of the model. More advanced models could similarly be employed without significant modification. The passive stress $F_p$ can be computed using linear models or orthotropic models, such as the orthotropic Holzapfel-Ogden (H-O) model. The H-O model is derived from considerations of the myocardial tissue structure, meaning that cardiac tissue shows different behavior whether it is stretched along the fiber direction, perpendicular to the fiber, etc. The H-O model comprises eight material constants, which are contained within an exponential stress-strain energy function. Reformulating the energy using multiplicative Jacobian energy decomposition (MJED) or Total Lagrangian Explicit Dynamics (TLED) formulation allows for efficient computation of patient-specific tissue biomechanics. Both the effect of arteries and atria on ventricular motion and a pericardium constraint are considered within the biomechanical model as mechanical boundary conditions, which account for the force vectors $F_b$. In the case in which the cardiac EP model is a cardiac electromechanics model, the method described above for personalizing the cardiac EP model can be modified to add a step of estimating patient-specific biomechanical tissue parameters (e.g., stiffness and maximum active stress) based a comparison observed heart movement in the dynamic cardiac medical images of the patient and simulated heart movement using the model of cardiac biomechanics to each iteration. In this case the cardiac electromechanics model simulates cardiac electromechanics (electrophysiology and biomechanics) and the cardiac electrophysiology parameters (e.g., diffusivity), cardiac biomechanics parameters (e.g., tissue stiffness and maximum active stress), and the line of block parameters are estimated based on the simulated cardiac electromechanics and the cardiac images and body potentials.

Returning to FIG. 2, at step 210, the personalized electrical diffusivity values and the simulated cardiac electrophysiology are output. The personalized (patient-specific) regional electrical diffusivity values can be output by displaying the values on a display device. In an exemplary implementation, the personalized electrical diffusivity parameters can be visualized by generating a 3D map of the patient's heart showing the spatially varying electrical diffusivity parameters and displaying the 3D diffusivity map on a display device. For example, the spatially varying personalized diffusivity parameters can be visualized by color coding the extracted mesh of the patient's heart based on the diffusivity value at each point on the mesh. The personalized electrical diffusivity parameters are also stored as the diffusivity parameters of a patient-specific computational cardiac EP model, which can then be used to perform patient-specific cardiac EP simulations, as described in step 108 of FIG. 1. In addition to the personalized electrical diffusivity values, the location and the extent of the line of block of the patient is also output. The 3D electrical diffusivity map will show the line of block, as the diffusivity values of endocardial points in the line of block will be lower from the other endocardial diffusivities. The calculated strain maps and mechanical activation map can also be output, for example, by displaying the strain maps and the mechanical activation map on a display device. The simulated electrophysiology can be visualized by generating 3D maps of the patient's heart showing the simulated action potentials over time.

As described above, the method of FIG. 2 estimates patient-specific cardiac electrical parameters based on strain maps extracted from dynamic cardiac images. According to a possible embodiment of the present invention, this method can be performed during one physiological state of the patient (e.g., at rest), or can be performed multiple times during various physiological states of the patient (e.g., at rest and at various levels of stress). Performing this method at various physiological states of the patient enables the estimation of restitution curve parameters for patient based on the simulated electrophysiology of the patient at the different physiological states. For example, the amount of shortening of the action potential duration with respect to the heart rate can be used to personalize ion channel parameters for the patient.

Although the method of FIG. 2 is described as performing the cardiac EP simulation using LBM-EP to solve a Mitchell-Schaeffer cardiac electrophysiology model, it is to be understood that the framework described herein can be used with any electrophysiology model (e.g., Mitchell-Schaeffer, TenTusscher, Fenton-Karma, etc.) or any solver (LBM, finite element, finite difference, etc.). As described above, the method of FIG. 2 uses ECG measurements of the patient to personalize the electrical diffusivity parameters. This method can be extended to a case in which invasive electrocardiography mapping or body surface potential mapping is available. In this case, the electrical depolarization is compared with the invasive electrocardiography mapping or the body surface potential mapping data and the strain maps together during the optimization process. The method of FIG. 2 can also be extended to a case in which only strain maps are available without any electrocardiography measurements. In this case, the speed of activation is estimated from the mechanical activation map and used to calculate the speed of the electrical wave, which is then used to estimate the speed electrical diffusivity, which can be used in the optimization process in place of the ECG measurements. Although the method of FIG. 2 describes the use of strain maps derived from dynamic cardiac images to personalize the electrical diffusivity parameters, the method can be similarly applied to cases in which other mechanical maps are used, such as motion, velocity, tissue Doppler imaging, etc.

Figure 7:
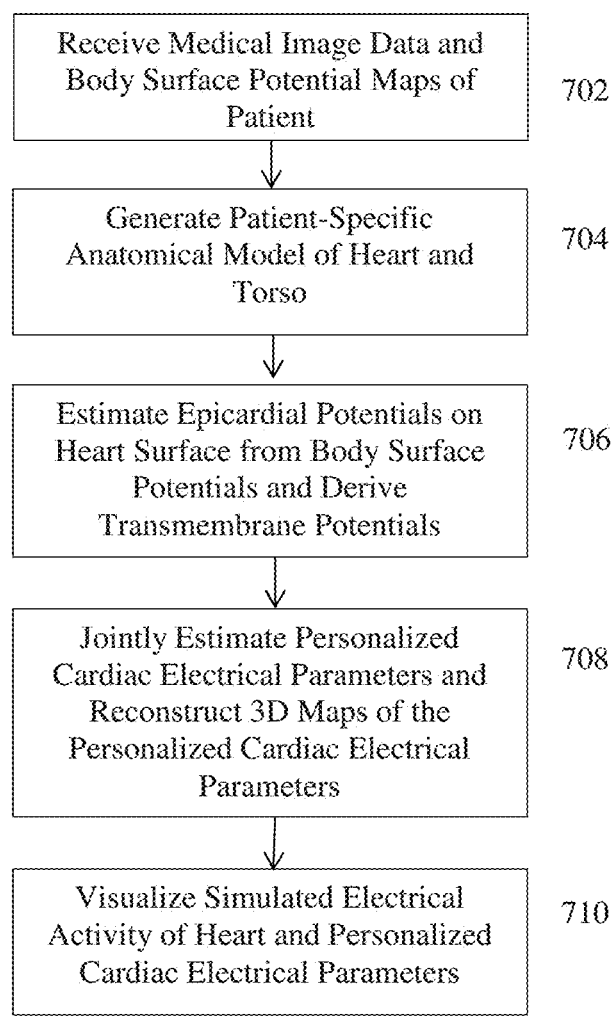
FIG. 7 illustrates a method of estimating patient-specific electrical properties of the heart according to a second embodiment of the present invention.
Figure 8:
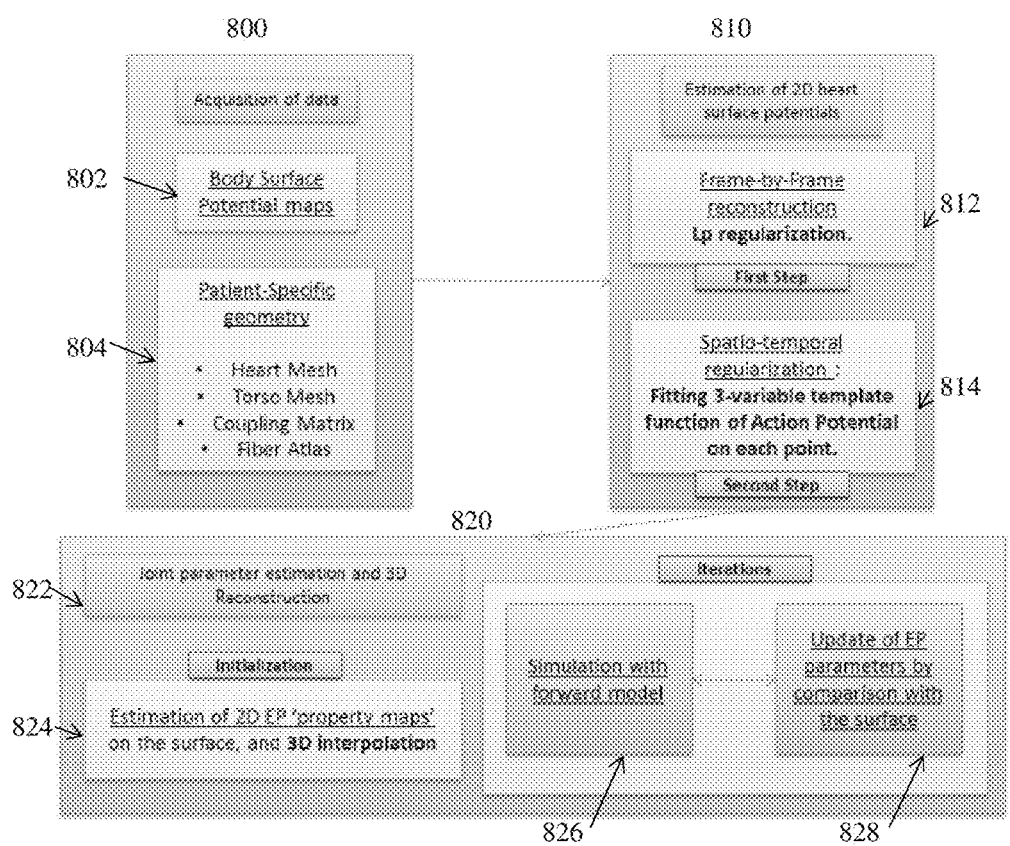
FIG. 8 is a functional block diagram illustrating a framework for performing the method of FIG. 7 according to an embodiment of the present invention.

FIG. 7 illustrates a method of estimating patient-specific electrical properties of the heart according to a second embodiment of the present invention. The method of FIG. 7 estimates patient-specific electrical properties of the heart based on medical images and measured body surface potentials of a patient. This embodiment combines body surface potential measurements acquired using body surface potential mapping or standard electrocardiogram, with a computational model of cardiac EP in order to visualize volumetric 3D heart potentials on the whole myocardium and quantify EP regional parameters of the heart and improve the accuracy of the patient-specific cardiac EP model. The method of FIG. 7 can be used to perform step 106 of FIG. 1 and generate a patient-specific computational cardiac EP model. Moreover, the method of FIG. 7 estimates cardiac electrical parameters of the patient that provide important information and can be employed as new physiological parameters for diagnostic and planning use, even without further simulations using the computational cardiac EP model. FIG. 8 is a functional block diagram illustrating a framework for performing the method of FIG. 7 according to an embodiment of the present invention.

Referring to FIG. 7, at step 702, medical image data and body surface potential measurements of the patient are received. The medical image data can be cardiac image data acquired using any type of medical imaging modality, such as computed tomography (CT), three-dimensional rotational angiography, magnetic resonance imaging (MRI), ultrasound (US), etc., provided that the heart is visible in the medical image data. In an advantageous implementation, the medical image data includes at least one 3D image of the patient's heart and at least one 3D image of the patient's torso. The medical image data can be received directly from an image acquisition device, such as a CT scanner, a C-arm image-acquisition device, an MRI scanner, or an US scanner, or the medical image data can be received by loading previously stored cardiac image data of the patient.

Body surface potential maps are acquired using Body Surface Mapping (BSM), which is a non-invasive method in electrical signals are simultaneously recorded from a large number of leads are placed on the torso of the patient. Typically, BSM records electrical signals (body surface potentials) from hundreds of leads on the torso of the patient. Any BSM system can be used. In fact, standard 12-lead ECG could also be employed, although at the price of potentially lower accuracy. The exact position of the leads on the torso of the patient with respect to the heart is obtained through imaging, for example with CT imaging or by using a 3D camera, such as Kinect. The body surface potential maps can be received directly from the BSM leads or can be received by loading previously stored body surface potential maps of the patient. As shown in FIG. 8, acquisition of data is performed at block 800 and includes acquisition of body surface potential maps in block 802.

Returning to FIG. 7, at step 704, a patient-specific anatomical model of the heart and the torso is generated from the medical image data of the patient. As shown in FIG. 8, the acquisition of data in block 800 includes acquisition of patient-specific geometry in block 804, which includes a heart mesh, torso mesh, coupling matrix the describes a coupling relationship between the heart mesh and the torso mesh, and a fiber atlas that provides a mapping of myocardium fibers on the heart mesh. Fibers could be also measured in-vivo with recent diffusion tensor magnetic resonance imaging. The patient-specific anatomical heart model, including the heart mesh, scar and border zones (segmented for instance on delayed enhancement MRI) labeled on the heart mesh, and the mapping of the myocardium fibers to the heart mesh, can be generated as described above in connection with step 104 of FIG. 1. In order to generate the patient-specific anatomical model of the torso (torso mesh), the boundaries of the torso and optionally the lungs, muscles, and bones can be segmented in a 3D image of the torso using machine learning techniques or other image segmentation techniques. The contours representing the torso boundaries are then fused to form a volumetric 3D mesh representing the torso.

An electrical model of diffusion in the torso is used to describe the coupling relationship between the heart and the torso. Electrical potentials on the torso can be calculated from cardiac potentials by first inferring extra-cellular potentials from the transmembrane potentials on the epicardium, and then solving a Poisson equation using the boundary element method (BEM), as shown in Equation (4) above. Accordingly, the electrical coupling between the heart mesh and the torso mesh can be modeled by the linear relationship $\forall t, Y_t = T*X_t$, where $X_t(x)$ denotes the extra-cellular potentials on the epicardium, $Y_t(x)$ denotes the torso potentials, and T is the coupling matrix or "transformation matrix" obtained by boundary element discretization of the heart-torso geometry and solving for the Poisson equation for electrical potentials.

At step 706 of FIG. 7, epicardial extra-cellular potentials on the heart surface are estimated from the body surface potential maps of the patient and transmembrane potentials on the heart surface are estimated from the extra-cellular potentials. As shown in FIG. 8, the estimation of 2D heart surface potentials, on the epicardium, is performed in block

810. Unfortunately, due to a loss of information through the torso, the coupling matrix T is non-invertible and this relationship cannot be used to uniquely recover the extra-cellular potentials on the epicardium surface from the torso potentials. Accordingly, block 810 of FIG. 8 shows a two-step method for reconstructing the epicardial extra-cellular potentials on the heart surface according to an advantageous embodiment of the present invention. The first step, block 812 performs frame-by-frame reconstruction of the extra-cellular potentials at the epicardium surface. The second step, block 814, infers the trans-membrane action potential at the epicardium trough spatio-temporal regularization and template matching based on a shape of action potential of the transmembrane potentials in the heart.

In the first step (block 812), the epicardial extra-cellular potentials are reconstructed frame-by-frame with spatial regularization, where each frame corresponds to a respective time step. An approximate map of extra-cellular potentials is reconstructed independently for each frame by solving the following "regularized problem":

$$\forall t, X(t) = \operatorname{argmin} \| Y_t - T^* X \|_{Lq} + \alpha \cdot \| V \cdot X \|_{Lp}. \quad (5)$$

The optimization of equation (5), which is "Lp regularized" and "Lq optimized", can be achieved by using Iteratively Reweighted Least Square and the value of p, q, and a can be chosen using a cross-validation approach depending on information on the torso potential map and prior knowledge on the state of the heart, such as knowledge of the presence of a propagating front where all locations are in a repolarizing state.

In the second step (block 814), the resulting approximate maps of epicardial extra-cellular potentials obtained in the first step are post-processed to derive transmembrane potentials on the epicardium and perform spatio-temporal regularization of the transmembrane potentials using knowledge of the "action potential" shape of the transmembrane potentials in the myocardium. This step uses the transmembrane potentials to provide temporal coherence for the estimated epicardial extra-cellular potentials. In an advantageous implementation, a mono-domain formulation of front propagation can be used, although the approach described herein can be applied on bi-domain formulations of cardiac electrocardiography as well. In the mono-domain framework, a first approximation of the relationship between the extra-cellular potential E(x, t) and transmembrane potential P(x, t) can be expressed as:

$$E(x,t) = \mu^*(f(t) - P(x,t)), \quad (6)$$

where $\mu$ is an anisotropy factor of the mono-domain model and $f(t)$ is proportional to the mean of the trans-membrane potential over the whole heart at a given time t. The transmembrane potential can be modeled in one point x with 3 parameters, which are the action potential duration APD (x), the amplitude of the action potential AAD(x), and the activation time of the cell AT(x). The template function TP of an action potential with an amplitude of 1 mV, a duration of 500 ms, and an activation time of 0 ms is used, so that the transmembrane potential on one point x in the myocardium is written as:

$$P(x, t) = TP\left(0.5 * \frac{(t - AT(x))}{APD(x)}\right) * AAD(x). \quad (7)$$

Over the whole epicardial surface, some regularity can be assumed in the AT, APD, and AAD maps. In particular, it can be assumed that the activation time is a piece-wise continuous function of the position on the heart mesh and that the action potential duration and amplitude are also piece-wise continuous values over the heart mesh, taking different values in the myocardium, in scar zones, or in border zones for instance. Action potential duration gradients can easily be incorporated.

The estimation and spatio-temporal regularization of the transmembrane potentials can be performed using an algorithm that jointly estimates the APD map, the AT map, the AAD map, and the function $f$ with a mathematical method based on Expectation-Maximization methods and pattern matching. As used herein, piecewise L2-regularization (PW-L2) denotes the process of performing L2-regularization independently inside each zone (scar zone, border zone, and myocardium zone) previously segmented from the medical image data and labeled on the heart mesh. According to an advantageous implementation, the algorithm can be performed as follows:

Initialize of the AAD map and the AT map by fitting the "extreme derivative point" of E(x, t) (i.e., minima or maxima of the extra-cellular potentials over time), initialize of the APD map at "QT duration-QRS duration" derived from the body surface potential measurements, and perform piecewise L2-regularization over the heart mesh.

Initialize $f(t)$ as the mean of E(x, t)+P(x, t) over the epicardial surface, weighted by a correlation coefficient between P x, t) derivatives and E(x, t) to give more weights to the correctly fitted trans-membrane potentials, and perform L2-regularization of $f(t)$ over time.

Iterate between the two following steps:
Refine the estimate of the transmembrane potentials P(x, t) on the epicardial surface by performing piecewise L2-regularization of the AAD, AT, and APD maps by optimizing each point in the following cost function:

$$\operatorname{argmin}_{AAD, AT, APD} \Sigma_x \left\| P(x, t) - AAD(x) * TP\left(\frac{t - AT(x)}{2 * APD(x)}\right) \right\|_{Lp} +$$
$$\| AAD(x) \|_{PW-L2} + \| APD(x) \|_{PW-L2} + \| AT(x) \|_{PW-L2}.$$

Estimate $f(t)$ as the mean of E(x, t)+P(x, t) over the surface of the heart mesh, weighted by the correlation coefficient between P(x, t) derivatives and E(x, t), and perform L2-regularization of $f(t)$ over time.

The final two steps of the algorithm can be iterated until convergence of the, AAD, and AT maps and $f$, or these steps can be iterated for a predetermined number of iterations. The above algorithm obtains a complete realistic representation of the epicardial trans-membrane surface potentials over time with a consistent action-potential shaped function of time in each point of the epicardial surface that can then be used to link with a forward model of cardiac EP to estimate volumetric patient-specific electrical parameters of the cardiac EP model.

Figure 9:
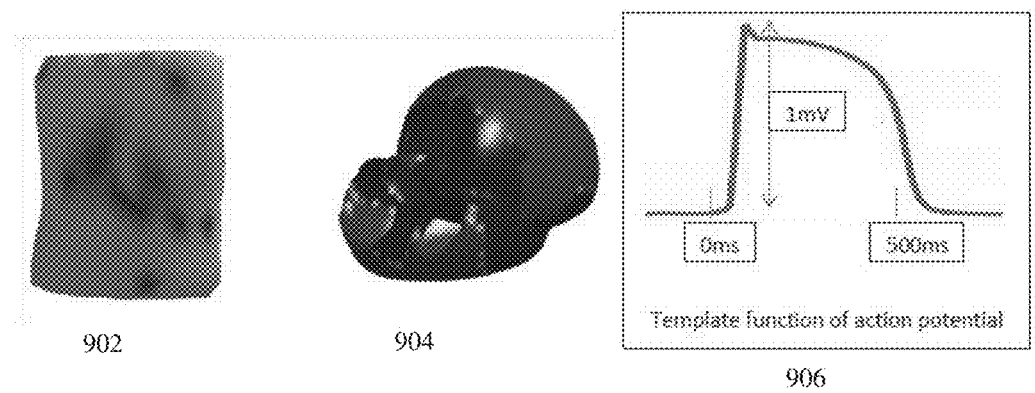
FIG. 9 illustrates exemplary results of the reconstructing epicardial potentials on a heart surface from torso potentials.

FIG. 9 illustrates exemplary results of the reconstructing epicardial trans-membrane potentials on a heart surface from torso potentials. As shown in FIG. 9, image 902 shows a visualization of torso potentials on a 3D torso mesh and image 904 shows a visualization of epicardial potentials on a surface of a 3D heart mesh that were reconstructed from the torso potentials. Image 906 shows the template function TP of action potential used in the spatio-temporal regularization of the epicardial potentials estimated from the surface potentials.

Returning to FIG. 7, at step 708, personalized cardiac electrical parameters are estimated and 3D (i.e. volumetric) maps of the cardiac electrical potentials are reconstructed. From the realistic representation of epicardial trans-membrane potentials on the heart surface, a computational cardiac EP model is used to reconstruct 3D volumetric transmembrane potentials inside the heart by iteratively estimating the cardiac electrical parameters inside the myocardium, simulating the electrical activity with the estimated cardiac electrical parameters, and comparing the transmembrane epicardial potentials on the heart surface resulting from the simulation with the reconstructed transmembrane epicardial surface potentials calculated in step 706, as described in the previous paragraphs. The cardiac EP model can be implemented as described above in connection with step 208 of FIG. 2. As described above, the cardiac EP model can simulate cardiac EP over time by calculating the transmembrane potential at each node within the myocardium of the anatomical heart model using the Lattice-Boltzmann Method for Electrophysiology (LBM-EP) to solve a cardiac electrophysiology model, such as a Mitchell-Schaeffer model, at each node. As shown in FIG. 8, joint cardiac electrical parameter estimation and 3D reconstruction of the potentials in the heart is performed in block 820, and includes initialization of the cardiac electrical properties in block 822 and iterations of simulation with the forward cardiac EP model (block 824) and updating of the EP parameters (cardiac electrical parameters) by comparison of the simulated transmembrane epicardial potentials on the heart surface with the transmembrane epicardial potentials on the heart surface reconstructed from the measured body surface potential maps.

In order to initialize values for spatially varying cardiac electrical parameters (block 822), a surface estimation (E1) is generated including 2D property maps of local repolarization time, amplitude, and diffusivity on the surface of the heart model. The activation time map of the derived transmembrane potentials is used to estimate an 'apparent' value of local electrical conductivity, which is then related to the electrical diffusivity on the surface. The electrical diffusivity on the surface is used with the local 3D direction of the front to approximate the parameters of the diffusivity tensor along the main direction of the fiber. The direction and anisotropy ratio of the fiber is known from the personalized anatomical heart model. The action potential duration of the derived transmembrane potentials is used to estimate the local value of repolarization time and the corresponding parameter in the cell model used (for example $\tau_{close}$ in the Mitchell-Schaeffer model). The action potential amplitude of the derived transmembrane potentials is used to personalize the voltage scaling factor of the cell model. In a case in which we are studying ventricular tachycardia, or a pacemaker induced electrical activity, the epicardial activation map can be used to identify the position of the pacemakers or the source of ventricular tachycardia. Once the 2D property maps are generated, the 2D maps are interpolated over the 3D heart model to generate an estimation (E2) of 3D maps of the cardiac electrical parameters. The 3D maps of the cardiac electrical parameters are initialized by supposing that the values inside the myocardium are the same as the closest point on the heart surface, except in cases in which we have insight on the tissue structure that contradicts the value. For example, at nodes in the heart model labeled as in a scar zone based on image segmentation, the electrical diffusivity value is zero.

Once the values of the cardiac electrical properties (e.g., diffusivity, action potential duration, and action potential amplitude) are initialized for all nodes in the myocardium, the following two steps are iterated to jointly estimate patient-specific cardiac electrical parameters and reconstruct 3D maps of the patient-specific electrical properties: (1) simulating cardiac electrophysiology with the computational cardiac EP model with the estimation (E2) of the 3D maps of the cardiac electrical properties as an input to the cardiac EP-model; and (2) calculating a difference between the simulated activation map on the epicardial surface resulting from the cardiac EP simulation and the reconstructed activation map generated from the measured torso potentials in the body surface potential mapping, and updating the estimation (E2) of the 3D maps of the cardiac electrical properties so that the difference decreases in the following iteration. More information such as global QRS duration, QT duration could also be employed to further constrain the problem. The cardiac electrophysiology simulation is performed as described above in connection step 208 of FIG. 2, and the simulated activation map on the heart surface is generated from the simulated transmembrane potentials. According to an advantageous implementation, the 3D maps of the cardiac electrical properties can be updated by jointly applying mathematical optimization methods, such as derivative-free local optimization, genetic algorithms, or more complex methods like forward-backward analysis from differential equations theory. The above steps can be iterated until convergence (i.e., the difference between the simulated and reconstructed activation maps is less than a threshold value), or for a predetermined number of iterations. This results in patient-specific spatially varying cardiac electrical parameters over the 3D heart model, which when input to the cardiac EP model, provide a patient-specific cardiac EP model that can be used to perform patient-specific cardiac EP simulations. The final iteration of the simulation step simulates transmembrane potentials in the heart using the patient-specific cardiac electrical parameters, and therefore provides a personalized 3D reconstruction of the electrophysiological activity of the heart. As described above, the patient-specific anatomical heart model can include areas labeled with particular tissue states, such as scar and border zones, which are identified using image segmentation techniques. In a possible implementation, the cardiac electrical parameters for such areas can be constrained to predetermined values (e.g., values indicating little or no electrical conductivity) based on the particular tissue state.

As described above, in step 708, personalized cardiac electrical parameters are estimated based on electrophysiology simulations using a computational cardiac EP model. According to a possible embodiment, the cardiac EP model may be computed on a moving mesh, obtained by tracking the heart on medical images. In another possible embodiment, the cardiac EP model may be a cardiac electromechanics model, which couples a model of cardiac biomechanics to the model of cardiac electrophysiology to simulate cardiac electrophysiology and cardiac biomechanics (cardiac movement) over a period of time. The cardiac electromechanics model can be implemented as described above in connection with step 208 of FIG. 2. In the case in which the cardiac EP model is a cardiac electromechanics model, the method described above for personalizing the cardiac EP model can be modified such that patient-specific biomechanical tissue parameters (e.g., stiffness and maximum active stress) of the mode of cardiac biomechanics are estimated based a comparison observed heart movement in the dynamic cardiac medical images of the patient and simulated heart movement using the model of cardiac biomechanics in each iteration. In this case, the cardiac electromechanics model simulates cardiac electromechanics (electrophysiology and biomechanics) and the cardiac electrophysiology parameters (e.g., diffusivity, action potential duration, and action potential amplitude) and cardiac biomechanics parameters (e.g., tissue stiffness and maximum active stress) are estimated based on the simulated cardiac electromechanics. Using a moving mesh will allow more accurate estimation of cardiac repolarization parameters (e.g. APD, etc.), which can be affected by cardiac motion.

Returning to FIG. 7, at step 710, the 3D volumetric maps of the cardiac electrical parameters are output. These 3D maps provide the cardiac electrical parameters throughout the myocardium wall and not only on the epicardial surface. The 3D maps of the cardiac electrical parameters (e.g., diffusivity, action potential duration, action potential amplitude) can be output by displaying the 3D volumetric maps on a display device. In an exemplary implementation, the 3D volumetric maps of the personalized electrical diffusivity parameters can be visualized on a rendering of the patient's heart that is displayed on the display device. For example, the spatially varying personalized cardiac electrical parameters can be visualized by color coding the extracted mesh of the patient's heart based on the diffusivity value at each point on the mesh. The 3D maps of the personalized cardiac electrical parameters are also stored as the corresponding parameters of the patient-specific computational cardiac EP model, which can then be used to perform patient-specific cardiac EP simulations, as described in step 108 of FIG. 1. In addition to the 3D maps of the personalized cardiac electrical parameters, maps of the epicardial potentials on the surface of the heart and/or the simulated transmembrane potentials computed using the patient-specific cardiac EP model can also be displayed. Other EP maps, such as an activation map, can also be visualized and displayed on the display device.

The method of FIG. 7 estimates patient-specific cardiac electrical parameters based on reconstructed epicardial potentials from measured body surface potentials (dense measurements or standard 12-lead ECG). According to a possible embodiment, FIG. 7 can be modified to further tune the patient-specific cardiac electrical parameters based on dynamic cardiac images using the method of FIG. 2, described above.

As described above, the method of FIG. 7 uses body surface potential maps acquired using BSM to reconstruct epicardial potentials on the surface of the heart in order to estimate patient-specific cardiac electrical parameters of the cardiac EP model throughout the myocardium (volumetric). It is to be understood that the present invention is not limited to BSM measurements and any body surface potential (torso potential) measurements can be used. For example, the method of FIG. 7 can be performed using body surface potentials acquired from standard 12-lead ECG recordings, or with 12 leads placed in different positions selected to have the most insight on a specific myocardial electrical activity. The method of FIG. 7 can also be extended to cover cases in which multiple recordings performed at different times are combined to analyze the same phenomena, such as sinus rhythm or lead-induced front propagation in CRT. The method of FIG. 7 can also be extended such that the personalization of the EP parameters of a local region of the heart is iteratively improved using multiple phenomena (e.g., combining ventricular tachycardia and sinus rhythm). This can for instance help estimate the restitution curve (i.e. how much the action potential shortens with respect to the heart rate).

Figure 10:
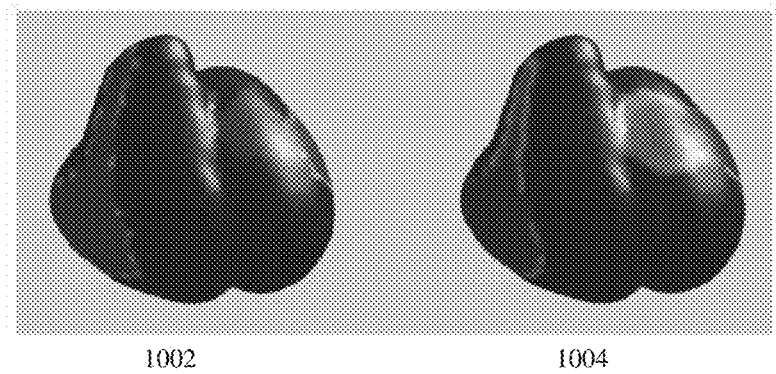
FIG. 10 illustrates exemplary results of reconstructing epicardial potentials on the heart surface from ECG measurements.
Figure 11:
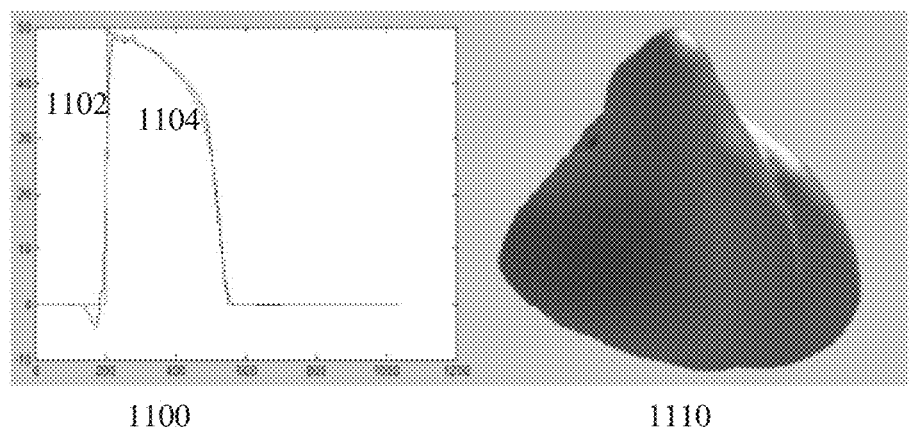
FIG. 11 illustrates results of reconstructing an activation map after action potential duration regularization.

FIG. 10 illustrates exemplary results of reconstructing epicardial potentials on the heart surface from ECG measurements. As shown in FIG. 10, image 1002 shows a visualization of reconstructed epicardial surface potentials from ECG measurements that show front propagation around a scar (no-diffusion zone), and image 1004 shows a visualization of ground truth epicardial potentials on the heart surface. FIG. 11 illustrates results of reconstructing an activation map after action potential duration regularization. As shown in FIG. 11, image 1100 shows fitting of the template action potential function TP 1102 on a reconstructed action potential 1104, and image 1110 shows a visualization of the reconstructed activation map on the left ventricle.

Figure 12:
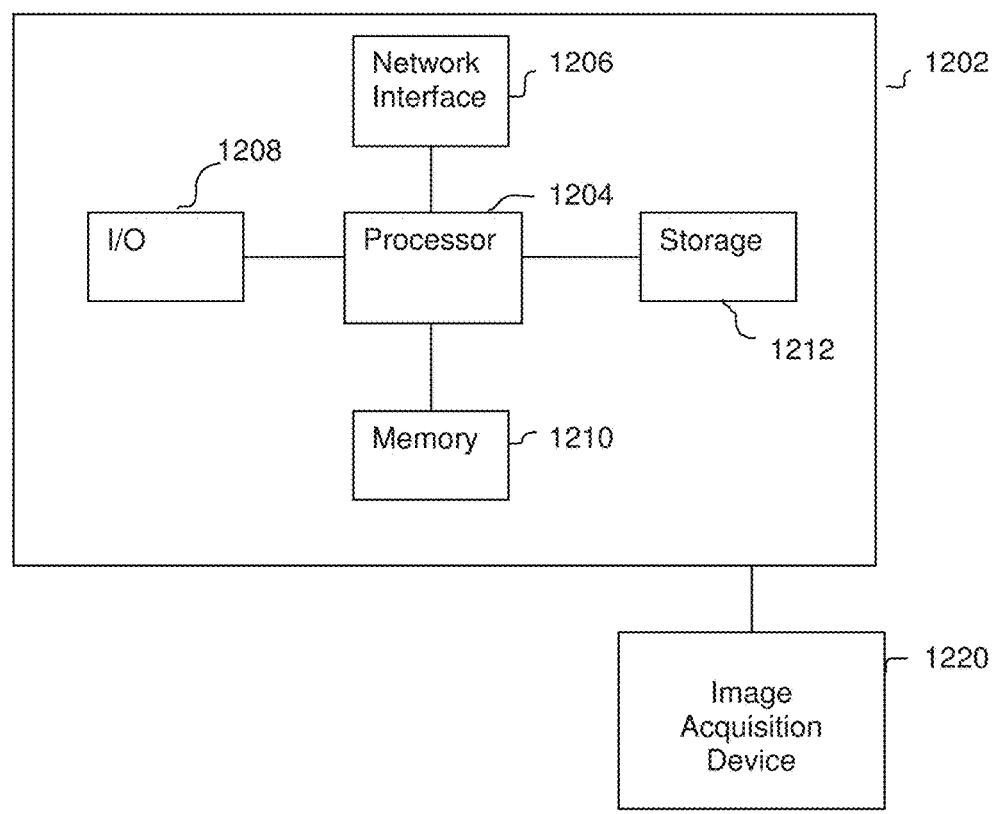
FIG. 12 is a high-level block diagram of a computer capable of implementing the present invention.

The above-described methods for patient-specific simulation of cardiac electrophysiology and estimating patient-specific cardiac electrical parameters can be implemented on a computer using well-known computer processors, memory units, storage devices, computer software, and other components. A high-level block diagram of such a computer is illustrated in FIG. 12. Computer 1202 contains a processor 1204, which controls the overall operation of the computer 1202 by executing computer program instructions which define such operation. The computer program instructions may be stored in a storage device 1212 (e.g., magnetic disk) and loaded into memory 1210 when execution of the computer program instructions is desired. Thus, the steps of the methods of FIGS. 1, 2, 3, 6, 7, and 8 may be defined by the computer program instructions stored in the memory 1210 and/or storage 1212 and controlled by the processor 1204 executing the computer program instructions. An image acquisition device 1220, such as a CT scanning device, C-arm image acquisition device, MR scanning device, Ultrasound device, etc., can be connected to the computer 1202 to input image data to the computer 1202. It is possible to implement the image acquisition device 1220 and the computer 1202 as one device. It is also possible that the image acquisition device 1220 and the computer 1202 communicate wirelessly through a network. In a possible embodiment, the computer 1202 may be located remotely with respect to the image acquisition device 1220 and may perform the method steps as part of a server or cloud based service. The computer 1202 also includes one or more network interfaces 1206 for communicating with other devices via a network. The computer 1202 also includes other input/output devices 1208 that enable user interaction with the computer 1202 (e.g., display, keyboard, mouse, speakers, buttons, etc.). Such input/output devices 1208 may be used in conjunction with a set of computer programs as an annotation tool to annotate volumes received from the image acquisition device 1220. One skilled in the art will recognize that an implementation of an actual computer could contain other components as well, and that FIG. 12 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for estimating patient-specific cardiac electrical properties from medical image data and non-invasive body surface potential measurements of a patient, comprising:
   generating a volumetric patient-specific anatomical heart model and a patient-specific anatomical torso model from medical image data of a patient and an electrical coupling model between the patient-specific anatomical heart model and the patient-specific anatomical torso model;
   estimating extra-cellular potentials on an epicardial surface of the patient-specific anatomical heart model from measured body surface potentials on a torso of the patient based on the electrical coupling model between the patient-specific anatomical heart model and the patient-specific anatomical torso model and estimating transmembrane potentials on the epicardial surface of the patient-specific anatomical heart model from the estimated extra-cellular potentials; and
   estimating spatially varying patient-specific cardiac electrical parameters for the patient by:
      initializing one or more cardiac electrical parameters of a computational cardiac electrophysiology model over the volumetric patient-specific anatomical heart model from the estimated transmembrane potentials on the epicardial surface of the patient-specific anatomical heart model;
      simulating cardiac electrophysiology over time at a plurality of nodes in the volumetric patient-specific anatomical heart model using the computational cardiac electrophysiology model, and
      adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology.

2. The method of claim 1, wherein estimating extra-cellular potentials on an epicardial surface of the patient-specific anatomical heart model from measured body surface potentials on a torso of the patient based on the electrical coupling model between the patient-specific anatomical heart model and the patient-specific anatomical torso model and estimating transmembrane potentials on the epicardial surface of the patient-specific anatomical heart model from the estimated extra-cellular potentials comprises:
   independently reconstructing approximate maps of the extra-cellular potentials on the epicardial surface of the patient-specific anatomical heart model for a plurality of time frames from measured body surface potentials of the patient for each of the plurality of time frames by solving a spatial regularization problem based on the electrical coupling model between the patient-specific anatomical heart model and the patient-specific anatomical torso model; and
   estimating the transmembrane potentials on the epicardial surface of the patient-specific anatomical heart model from the approximate maps of the extra-cellular potentials on the epicardial surface and performing spatio-temporal regularization of the transmembrane potentials of the epicardial surface based on a shape of an action potential modeled for the transmembrane potentials.

3. The method of claim 2, wherein estimating the transmembrane potentials on the epicardial surface of the patient-specific anatomical heart model from the approximate maps of the extra-cellular potentials on the epicardial surface and performing spatio-temporal regularization of the transmembrane potentials of the epicardial surface based on a shape of an action potential modeled for the transmembrane potentials comprises:
   initializing an action potential duration map, an activation time map, and an action potential amplitude map modeling action potential propagation of the transmembrane potentials on the epicardial surface based on the approximate maps of the extra-cellular potentials on the epicardial surface;
   initializing a function representing a relationship between the transmembrane potentials and the extra-cellular potentials based on transmembrane potentials estimated from the action potential duration map, the activation time map, and the action potential amplitude map using a template action potential function; and
   performing one or more iterations of the following steps:
      refining the action potential duration, activation time, and action potential amplitude maps using piecewise L2-regularized Lp-norm optimization, wherein the piecewise L2-regularized Lp norm optimization performs regularization independently in scar, border, and myocardium zones of the patient-specific anatomical heart model, as identified in the medical image data; and
      adjusting the function representing the relationship between the extra-cellular potentials and the transmembrane potentials based on transmembrane potentials estimated from the refined action potential duration, activation time, and action potential amplitude maps and performing regularization of the function over time.

4. The method of claim 1, wherein initializing one or more cardiac electrical parameters of a computational cardiac electrophysiology model over the volumetric patient-specific anatomical heart model from the estimated transmembrane potentials on the epicardial surface of the patient-specific anatomical heart model comprises:
   generating a surface estimation of each of the one or more cardiac electrical parameters on the surface of the patient-specific anatomical heart model based on the estimated transmembrane potentials on the epicardial surface of the patient-specific anatomical heart model; and
   generating a respective 3D map of each of the one or more cardiac electrical parameters over the volumetric patient-specific anatomical heart model by interpolating the respective surface estimation of each of the one or more cardiac electrical parameters over the volume of the myocardium in the patient-specific anatomical heart model.

5. The method of claim 4, wherein generating a surface estimation of each of the one or more cardiac electrical parameters on the surface of the patient-specific anatomical heart model based on the estimated transmembrane potentials on the epicardial surface of the patient-specific anatomical heart model comprises:

generating a 2D map of electrical diffusivity on the surface of the patient-specific anatomical heart model based on an activation time map of the estimated transmembrane potentials on the epicardial surface of the patient-specific anatomical heart model;

generating a 2D map of local depolarization time on the surface of the patient-specific anatomical heart model from an action potential duration map of the estimated transmembrane potentials on the epicardial surface of the patient-specific anatomical heart model; and generating a 2D map of action potential amplitude from an action potential amplitude map of the estimated transmembrane potentials on the epicardial surface of the patient-specific anatomical heart model.

6. The method of claim 4, wherein adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology comprises:

adjusting the respective 3D map for each of the one or more cardiac electrical parameters to reduce a difference between the simulated transmembrane potentials on the epicardial surface and the estimated transmembrane potentials on the epicardial surface.

7. The method of claim 1, wherein simulating cardiac electrophysiology over time at a plurality of nodes in the volumetric patient-specific anatomical heart model using the computational cardiac electrophysiology model comprises:

simulating transmembrane potentials over time within the volumetric patient-specific anatomical heart model using the computational cardiac electrophysiology model.

8. The method of claim 7, wherein simulating transmembrane potentials over time within the volumetric patient-specific anatomical heart model using the computational cardiac electrophysiology model comprises:

generating a Cartesian grid domain using the patient-specific anatomical heart model; and calculating transmembrane potential variation over time at each of a plurality of nodes within the myocardium in the Cartesian grid domain by computing a solution of the computational cardiac electrophysiology model for each of the plurality of nodes using a Lattice-Boltzmann method for electrophysiology.

9. The method of claim 1, wherein simulating cardiac electrophysiology over time at a plurality of nodes in the volumetric patient-specific anatomical heart model using the computational cardiac electrophysiology model comprises:

simulating transmembrane potentials over time within the volumetric patient-specific anatomical heart model and movement of the patient-specific anatomical heart model over time using a computational cardiac electromechanics model.

10. The method of claim 1, wherein simulating cardiac electrophysiology over time at a plurality of nodes in the volumetric patient-specific anatomical heart model using the computational cardiac electrophysiology model comprises:

computing cardiac electrophysiology on a moving mesh directly obtained from a tracked segmentation over a plurality of frames of a dynamic cardiac image sequence.

11. The method of claim 1, wherein adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology comprises:

adjusting the one or more cardiac electrical parameters of the computational cardiac electrophysiology model based on the estimated transmembrane potentials on the epicardial surface of the patient-specific anatomical heart model, the simulated transmembrane potentials resulting from simulating the cardiac electrophysiology, and cardiac motion estimated from dynamic cardiac images.

12. An apparatus for estimating patient-specific cardiac electrical properties from medical image data and non-invasive body surface potential measurements of a patient, comprising:

means for generating a volumetric patient-specific anatomical heart model and a patient-specific anatomical torso model from medical image data of a patient and an electrical coupling model between the patient-specific anatomical heart model and the patient-specific anatomical torso model;

means for estimating extra-cellular potentials on an epicardial surface of the patient-specific anatomical heart model from measured body surface potentials on a torso of the patient based on the electrical coupling model between the patient-specific anatomical heart model and the patient-specific anatomical torso model and estimating transmembrane potentials on the epicardial surface of the patient-specific anatomical heart model from the estimated extra-cellular potentials; and means for estimating spatially varying patient-specific cardiac electrical parameters for the patient, comprising:

means for initializing one or more cardiac electrical parameters of a computational cardiac electrophysiology model over the volumetric patient-specific anatomical heart model from the estimated transmembrane potentials on the epicardial surface of the patient-specific anatomical heart model;

means for simulating cardiac electrophysiology over time at a plurality of nodes in the volumetric patient-specific anatomical heart model using the computational cardiac electrophysiology model, and means for adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology.

13. The apparatus of claim 12, wherein the means for estimating extra-cellular potentials on an epicardial surface of the patient-specific anatomical heart model from measured body surface potentials on a torso of the patient based on the electrical coupling model between the patient-specific anatomical heart model and the patient-specific anatomical torso model and estimating transmembrane potentials on the epicardial surface of the patient-specific anatomical heart model from the estimated extra-cellular potentials comprises:

means for independently reconstructing approximate maps of the extra-cellular potentials on the epicardial surface of the patient-specific anatomical heart model for a plurality of time frames from measured body surface potentials of the patient for each of the plurality of time frames by solving a spatial regularization problem based on the electrical coupling model between the patient-specific anatomical heart model and the patient-specific anatomical torso model; and means for estimating the transmembrane potentials on the epicardial surface of the patient-specific anatomical heart model from the approximate maps of the extra-cellular potentials on the epicardial surface and performing spatio-temporal regularization of the transmembrane potentials of the epicardial surface based on a shape of an action potential modeled for the transmembrane potentials.

14. The apparatus of claim 12, wherein the means for initializing one or more cardiac electrical parameters of a computational cardiac electrophysiology model over the volumetric patient-specific anatomical heart model from the estimated transmembrane potentials on the epicardial surface of the patient-specific anatomical heart model comprises:

means for generating a surface estimation of each of the one or more cardiac electrical parameters on the surface of the patient-specific anatomical heart model based on the estimated transmembrane potentials on the epicardial surface of the patient-specific anatomical heart model; and means for generating a respective 3D map of each of the one or more cardiac electrical parameters over the volumetric patient-specific anatomical heart model by interpolating the respective surface estimation of each of the one or more cardiac electrical parameters over the volume of the myocardium in the patient-specific anatomical heart model.

15. The apparatus of claim 14, wherein the means for adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology comprises:

means for adjusting the respective 3D map for each of the one or more cardiac electrical parameters to reduce a difference between the simulated transmembrane potentials on the epicardial surface and the estimated transmembrane potentials on the epicardial surface.

16. A non-transitory computer readable medium storing computer program instructions for estimating patient-specific cardiac electrical properties from medical image data and non-invasive body surface potential measurements of a patient, the computer program instructions when executed by a processor cause the processor to perform operations comprising:

generating a volumetric patient-specific anatomical heart model and a patient-specific anatomical torso model from medical image data of a patient and an electrical coupling model between the patient-specific anatomical heart model and the patient-specific anatomical torso model;

estimating extra-cellular potentials on an epicardial surface of the patient-specific anatomical heart model from measured body surface potentials on a torso of the patient based on the electrical coupling model between the patient-specific anatomical heart model and the patient-specific anatomical torso model and estimating transmembrane potentials on the epicardial surface of the patient-specific anatomical heart model from the estimated extra-cellular potentials; and estimating spatially varying patient-specific cardiac electrical parameters for the patient by:

initializing one or more cardiac electrical parameters of a computational cardiac electrophysiology model over the volumetric patient-specific anatomical heart model from the estimated transmembrane potentials on the epicardial surface of the patient-specific anatomical heart model;

simulating cardiac electrophysiology over time at a plurality of nodes in the volumetric patient-specific anatomical heart model using the computational cardiac electrophysiology model, and adjusting the one or more cardiac electrical parameters of the computational cardiac electrophysiology model over the volumetric patient-specific anatomical heart model based on the estimated transmembrane potentials on the epicardial surface of the patient-specific anatomical heart model, and simulated transmembrane potentials on the epicardial surface of the patient-specific anatomical heart model resulting from simulating the cardiac electrophysiology.

17. The non-transitory computer readable medium of claim 16, wherein estimating extra-cellular potentials on an epicardial surface of the patient-specific anatomical heart model from measured body surface potentials on a torso of the patient based on the electrical coupling model between the patient-specific anatomical heart model and the patient-specific anatomical torso model and estimating transmembrane potentials on the epicardial surface of the patient-specific anatomical heart model from the estimated extra-cellular potentials comprises:

independently reconstructing approximate maps of the extra-cellular potentials on the epicardial surface of the patient-specific anatomical heart model for a plurality of time frames from measured body surface potentials of the patient for each of the plurality of time frames by solving a spatial regularization problem based on the electrical coupling model between the patient-specific anatomical heart model and the patient-specific anatomical torso model; and estimating the transmembrane potentials on the epicardial surface of the patient-specific anatomical heart model from the approximate maps of the extra-cellular potentials on the epicardial surface and performing spatio-temporal regularization of the transmembrane potentials of the epicardial surface based on a shape of an action potential modeled for the transmembrane potentials.

18. The non-transitory computer readable medium of claim 17, wherein estimating the transmembrane potentials on the epicardial surface of the patient-specific anatomical heart model from the approximate maps of the extra-cellular potentials on the epicardial surface and performing spatio-temporal regularization of the transmembrane potentials of the epicardial surface based on a shape of an action potential modeled for the transmembrane potentials comprises:

initializing an action potential duration map, an activation time map, and an action potential amplitude map modeling action potential propagation of the transmembrane potentials on the epicardial surface based on the approximate maps of the extra-cellular potentials on the epicardial surface;

initializing a function representing a relationship between the transmembrane potentials and the extra-cellular potentials based on transmembrane potentials estimated from the action potential duration map, the activation time map, and the action potential amplitude map using a template action potential function; and performing one or more iterations of the following steps:
refining the action potential duration, activation time, and action potential amplitude maps using piecewise L2-regularized Lp-norm optimization, wherein the piecewise L2-regularized Lp norm optimization performs regularization independently in scar, border, and myocardium zones of the patient-specific anatomical heart model, as identified in the medical image data; and adjusting the function representing the relationship between the extra-cellular potentials and the transmembrane potentials based on transmembrane potentials estimated from the refined action potential duration, activation time, and action potential amplitude maps and performing regularization of the function over time.

19. The non-transitory computer readable medium of claim 16, wherein initializing one or more cardiac electrical parameters of a computational cardiac electrophysiology model over the volumetric patient-specific anatomical heart model from the estimated transmembrane potentials on the epicardial surface of the patient-specific anatomical heart model comprises:

generating a surface estimation of each of the one or more cardiac electrical parameters on the surface of the patient-specific anatomical heart model based on the estimated transmembrane potentials on the epicardial surface of the patient-specific anatomical heart model; and generating a respective 3D map of each of the one or more cardiac electrical parameters over the volumetric patient-specific anatomical heart model by interpolating the respective surface estimation of each of the one or more cardiac electrical parameters over the volume of the myocardium in the patient-specific anatomical heart model.

20. The non-transitory computer readable medium of claim 19, wherein generating a surface estimation of each of the one or more cardiac electrical parameters on the surface of the patient-specific anatomical heart model based on the estimated transmembrane potentials on the epicardial surface of the patient-specific anatomical heart model comprises:

generating a 2D map of electrical diffusivity on the surface of the patient-specific anatomical heart model based on an activation time map of the estimated transmembrane potentials on the epicardial surface of the patient-specific anatomical heart model;

generating a 2D map of local depolarization time on the surface of the patient-specific anatomical heart model from an action potential duration map of the estimated transmembrane potentials on the epicardial surface of the patient-specific anatomical heart model; and generating a 2D map of action potential amplitude from an action potential amplitude map of the estimated transmembrane potentials on the epicardial surface of the patient-specific anatomical heart model.

* * * * *